(12) United States Patent
Dhaens

(10) Patent No.: US 11,541,797 B2
(45) Date of Patent: Jan. 3, 2023

(54) SYSTEMS AND METHODS FOR MINIMIZING MOTION SICKNESS IN VEHICLES

(71) Applicant: DRiV Automotive Inc., Lake Forest, IL (US)

(72) Inventor: Miguel Dhaens, Lommel (BE)

(73) Assignee: DRiV Automotive Inc., Skokie, IL (US)

( * ) Notice: Subject to any disclaimer, the term of this patent is extended or adjusted under 35 U.S.C. 154(b) by 362 days.

(21) Appl. No.: 16/751,602

(22) Filed: Jan. 24, 2020

(65) Prior Publication Data
US 2020/0238876 A1 Jul. 30, 2020

Related U.S. Application Data

(60) Provisional application No. 62/796,697, filed on Jan. 25, 2019.

(51) Int. Cl.
*B60N 2/90* (2018.01)
*A61M 21/00* (2006.01)
(Continued)

(52) U.S. Cl.
CPC ............ *B60N 2/976* (2018.02); *A61M 21/00* (2013.01); *B60G 17/06* (2013.01); *B60N 2/646* (2013.01);
(Continued)

(58) Field of Classification Search
CPC .......... B60N 2/976; B60N 2/646; B60N 2/68; B60N 2/501; A61M 21/00;
(Continued)

(56) References Cited

U.S. PATENT DOCUMENTS 6,419,647 B1 * 7/2002 Fujita .................. G09B 9/00
600/595
7,437,219 B2 10/2008 Bos
(Continued)

FOREIGN PATENT DOCUMENTS

CN 1880113 A 12/2006
CN 101172466 A 5/2008
(Continued)

OTHER PUBLICATIONS

Notification of Transmittal of International Search Report and Written Opinion of the International Searching Authority regarding International Application No. PCT/US2020/014932 dated Jun. 23, 2020 (12 pages).
(Continued)

*Primary Examiner* — Michael J Zanelli
(74) *Attorney, Agent, or Firm* — DRiV Automotive Inc.

(57) ABSTRACT

A motion sickness control system for a vehicle includes a vibrator. The motion sickness control system includes a sensor configured to measure vibration of the vehicle. The motion sickness control system includes a computer having a processor and a memory storing instructions executable by the processor to actuate the vibrator at a target frequency
(Continued)

based on the measured vibration of the vehicle. The target frequency attenuates the measured vibration of the vehicle.

17 Claims, 5 Drawing Sheets

(51) Int. Cl.
  *B60G 17/06* (2006.01)
  *B60N 2/64* (2006.01)
  *B60N 2/68* (2006.01)
  *B60R 11/04* (2006.01)

(52) U.S. Cl.
  CPC ............... *B60N 2/68* (2013.01); *B60R 11/04* (2013.01); *A61M 2021/0022* (2013.01); *A61M 2205/3303* (2013.01); *A61M 2205/3306* (2013.01); *A61M 2205/3327* (2013.01); *B60G 2400/102* (2013.01); *B60G 2400/104* (2013.01); *B60G 2400/90* (2013.01)

(58) Field of Classification Search
  CPC .. A61M 2021/0022; A61M 2205/3303; A61M 2205/3306; A61M 2205/3327; B60G 17/06; B60G 17/019; B60G 2400/102; B60G 2400/104; B60G 2400/90; B60G 2400/00; B60G 2400/91; B60G 2600/182; B60R 11/04; F16F 15/002; F16F 15/005
  See application file for complete search history.

(56) References Cited

U.S. PATENT DOCUMENTS

| | | | |
|---|---|---|---|
| 7,490,572 B2 | 2/2009 | Grober | |
| 7,722,526 B2 | 5/2010 | Kim | |
| 8,078,364 B2 | 12/2011 | Mabuchi | |
| 11,305,675 B2 * | 4/2022 | Duan | ..................... B60N 2/067 |
| 2017/0136842 A1 | 5/2017 | Anderson et al. | |
| 2018/0015842 A1 * | 1/2018 | Hardee | ................ B60N 2/0244 |
| 2019/0022347 A1 * | 1/2019 | Wan | ......................... A61B 5/18 |
| 2020/0062240 A1 * | 2/2020 | Marzorati | ......... B60W 50/0098 |

FOREIGN PATENT DOCUMENTS

| | | | | |
|---|---|---|---|---|
| CN | 104972932 B | | 9/2017 | |
| CN | 107848360 A | | 3/2018 | |
| EP | 3167927 A1 | | 5/2017 | |
| JP | H04129847 A | | 4/1992 | |
| JP | 2782937 B2 | * | 8/1998 | |
| JP | 2006027347 A | * | 2/2006 | ............ A61M 21/02 |
| KR | 20000009710 A | * | 2/2000 | ............ F16F 15/002 |

OTHER PUBLICATIONS

Chinese Office Action dated Nov. 10, 2022 regarding CN App. No. 202080010510.0 (9 pages) (English translation not available).

* cited by examiner

SYSTEMS AND METHODS FOR MINIMIZING MOTION SICKNESS IN VEHICLES

CROSS-REFERENCE TO RELATED APPLICATIONS

The subject patent application claims priority to, and all the benefits of, U.S. Provisional Patent Application No. 62/796,697 filed on Jan. 25, 2019, which is herein incorporated by reference in its entirety.

FIELD

The present disclosure relates to vehicles and more particularly to systems and methods for minimizing or preventing motion sickness of occupants of vehicles.

BACKGROUND

Shock absorbers (or dampers) are typically used in conjunction with automotive suspension systems or other suspension systems to absorb vibrations that occur during movement of the suspension system. In order to absorb these vibrations, automotive shock absorbers are generally connected between the sprung (body) and the unsprung (suspension/drivetrain) masses of a vehicle.

The shock absorbers, however, do not damp all of the vertical vibration of the vehicle. Some vertical vibration may cause motion sickness of vehicle occupants. It is desirable to provide a motion sickness control system to improve the riding experience of vehicle occupants.

BRIEF DESCRIPTION OF THE DRAWINGS

The present disclosure will become more fully understood from the detailed description and the accompanying drawings, wherein.

DETAILED DESCRIPTION

Figure 1:
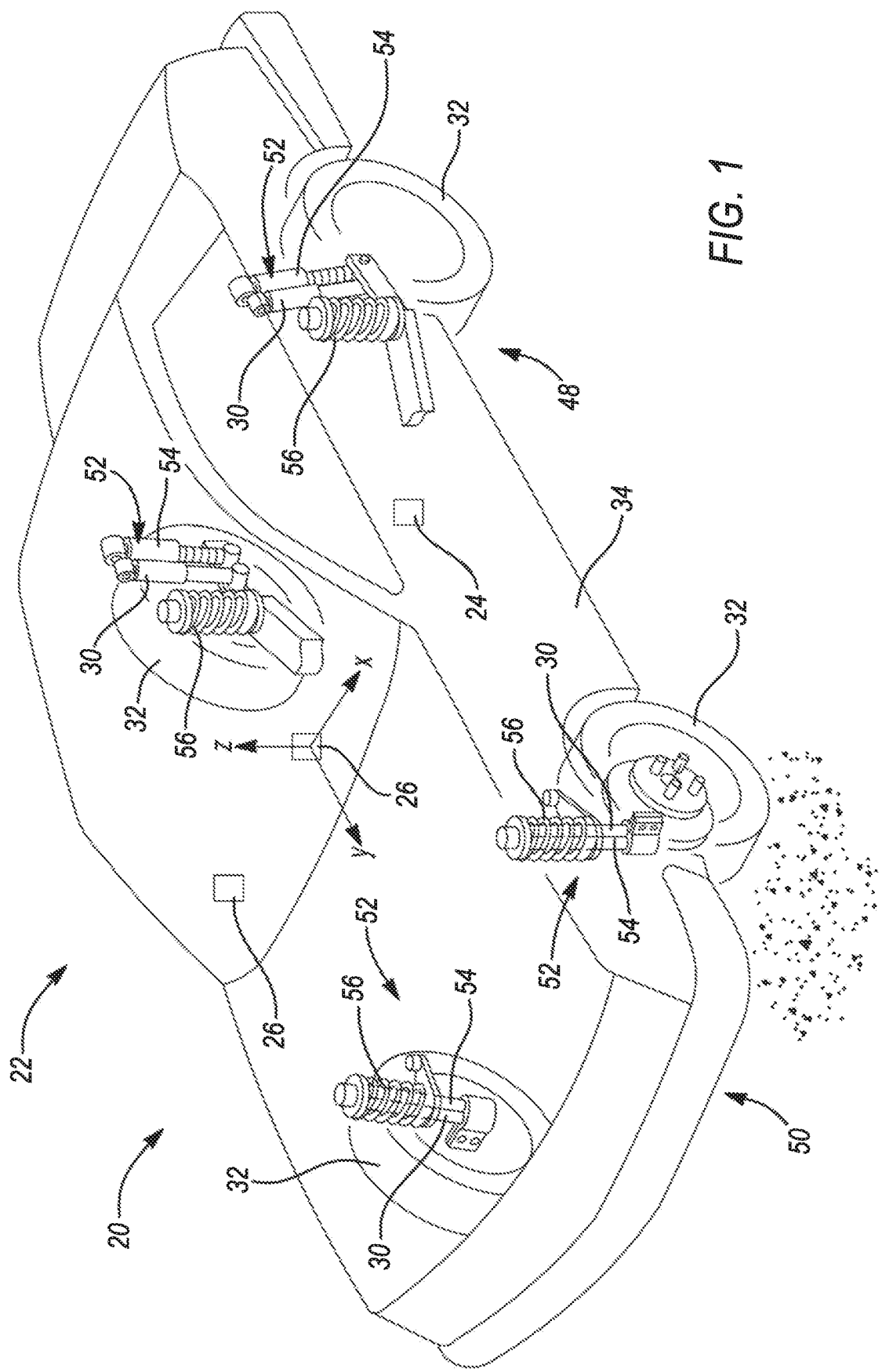
FIG. 1 is perspective view of an example vehicle having a seat and a motion sickness control system.
Figure 3:
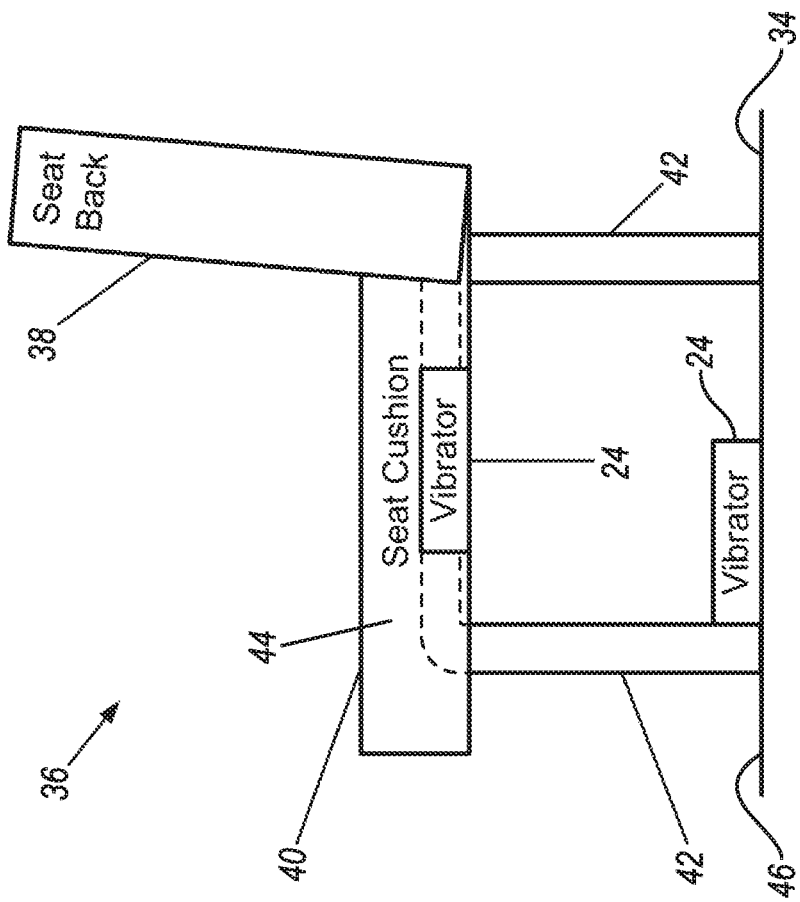
FIG. 3 is a side view of the seat.
Figure 2:
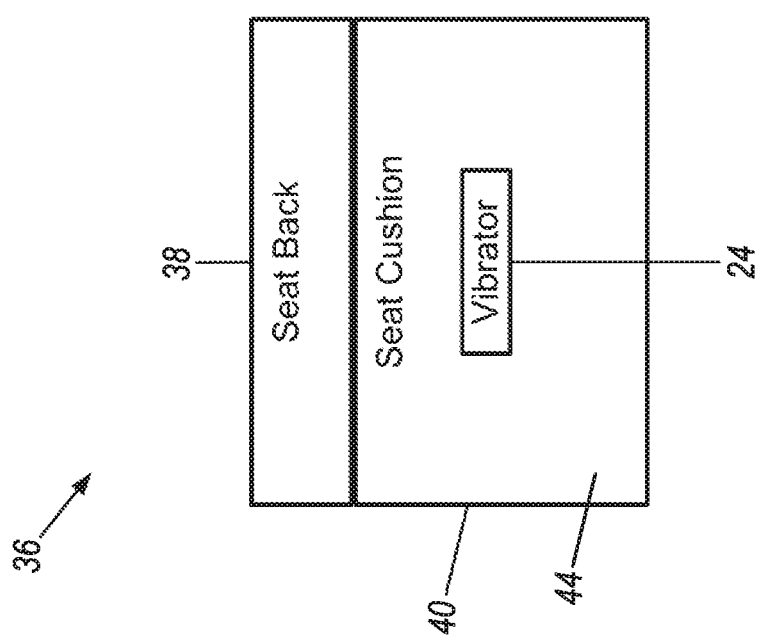
FIG. 2 is a top view of the seat.

A motion sickness control system for a vehicle includes a vibrator. The motion sickness control system includes a sensor configured to measure vibration of the vehicle. The motion sickness control system includes a computer having a processor and a memory storing instructions executable by the processor to actuate the vibrator at a target frequency based on the measured vibration of the vehicle. The target frequency attenuates the measured vibration of the vehicle.

The motion sickness control system may include a seat, the vibrator supported by the seat.

The seat may include a seat bottom having a cushion, and the vibrator may be supported within the cushion.

The seat may include a frame, and the vibrator may be fixed to the frame.

The motion sickness control system may include a vehicle body, the vibrator fixed to the vehicle body.

The sensor may be configured to measure an amplitude of the vibration of the vehicle, and the instructions may include instructions to actuate the vibrator at the target frequency upon determining the amplitude of the vibration is greater than a predetermined amplitude.

The sensor may be configured to measure an amplitude and a frequency of the vibration of the vehicle, and the instructions may include instructions to actuate the vibrator at a target amplitude and a target frequency based on the measured amplitude and frequency of the vibration.

The motion sickness control system may include a biometric sensor, and the instructions may include instructions to actuate the vibrator upon determining data from the biometric sensor is indicative of motion sickness.

The biometric sensor may be a camera configured to capture images of eyes of an occupant of the vehicle, and the instructions may include instructions to actuate to the vibrator upon determining that images from the camera include predetermined eye movement indicative of motion sickness.

The biometric sensor may be a heart rate sensor configured to measure a heart rate of an occupant of the vehicle, and the instructions may include instructions to actuate to the vibrator upon determining that a heart rate detected by the heart rate sensor includes a predetermined characteristic indicative motion sickness.

The biometric sensor may be a brainwave sensor configured to measure brainwaves of an occupant of the vehicle, and the instructions may include instructions to actuate to the vibrator upon determining that brainwaves detected by the brainwave sensor include a predetermined characteristic indicative of motion sickness.

The biometric sensor may be a perspiration sensor configured to measure perspiration of an occupant of the vehicle, and the instructions may include instructions to actuate to the vibrator upon determining that perspiration detected by the perspiration sensor includes a predetermined characteristic indicative of motion sickness.

The motion sickness control system may include an active damper, and the instructions may include instructions to actuate the active damper at a damper target based on the measured vibration of the vehicle, wherein the damper target attenuates the measured vibration of the vehicle.

The motion sickness control system may include an active damper, and the instructions may include instructions to predict a trajectory of the vehicle and to actuate the active damper based on the predicted trajectory to reduce motion sickness of an occupant of the vehicle.

The instructions may include instructions to actuate the active damper to attenuate lateral acceleration experienced by the occupant along the predicted trajectory.

A motion sickness control system for a vehicle includes an accelerometer configured to measure vertical acceleration of the vehicle. The motion sickness control system includes an active damper configured to damp vertical movement of a wheel of the vehicle. The motion sickness control system includes a computer having a processor and a memory storing instructions executable by the processor to actuate the active damper at a damper target based on the vertical acceleration detected by the accelerometer. The damper target attenuates the measured vertical acceleration of the vehicle.

The damper target may include a target damping coefficient, and the instructions may include instructions to control a damping coefficient of the active damper based on the target damping coefficient.

The instructions may include instructions to predict a trajectory of the vehicle and to actuate the active damper based on the predicted trajectory to reduce motion sickness of an occupant of the vehicle.

The instructions may include instructions to actuate the active damper to attenuate lateral acceleration experienced by the occupant along the predicted trajectory.

The motion sickness control system may include a vibrator, and the instructions may include instructions to actuate the vibrator at a target frequency based on the measured vertical acceleration of the vehicle, the target frequency attenuating the measured vertical acceleration of the vehicle.

With reference to FIGS. 1-4, a motion sickness control system 20 for a vehicle 22 includes a vibrator 24. The motion sickness control system 20 includes a sensor 26 configured to measure vibration of the vehicle 22. The motion sickness control system 20 includes a computer 28 having a processor and a memory storing instructions executable by the processor to actuate the vibrator 24 at a target frequency based on the measured vibration of the vehicle 22. The target frequency attenuates the measured vibration of the vehicle 22. Additionally, or alternately, the motion sickness control system 20 may include an accelerometer configured to measure vertical acceleration of the vehicle 22 and an active damper 30 configured to damp vertical movement of a wheel 32 of the vehicle 22. The memory may additionally, or alternatively, store instructions executable by the processor to actuate the active damper 30 at a damper target based on the vertical acceleration detected by the accelerometer. The damper target attenuates the measured vertical acceleration of the vehicle 22.

The motion sickness control system 20 cancels or attenuate vertical vibration and other forces that may cause motion sickness. Vehicle occupants may experience motion sickness during use of the vehicle 22 when vibration in a vertical (Z) direction around or within a predetermined frequency range is experienced for a period of time. For example, vertical vibration at or near a predetermined frequency (e.g., 0.7 Hz) may cause motion sickness of vehicle occupants. The vibration generated by the vibrators 24 may cancel or attenuate the vertical vibration and prevent or minimize motion sickness by vehicle 22 occupants. The active dampers 30 may cancel or attenuate vertical vibration and other forces that may cause motion sickness, e.g., via a controlled damping coefficient and or body angle of the vehicle 22.

The vehicle 22 may be any type of passenger or commercial automobile such as a car, a truck, a sport utility vehicle, a crossover vehicle, a van, a minivan, a taxi, a bus, etc.

The vehicle 22 includes a body 34 and a frame. The body 34 and frame may be of a unibody construction. In the unibody construction, the body 34, e.g., rockers, serves as the vehicle frame, and the body 34 (including the rockers, pillars, roof rails, etc.) is unitary, i.e., a continuous one-piece unit. As another example, the body 34 and frame may have a body-on-frame construction (also referred to as a cab-on-frame construction). In other words, the body 34 and frame are separate components, i.e., are modular, and the body 34 is supported on and affixed to the frame. Alternatively, the body 34 and frame may have any suitable construction. The body 34 and/or the frame may be formed of any suitable material, for example, steel, aluminum, etc.

The vehicle 22 includes one or more seats 36. Each seat 36 may include a seat back 38 and a seat bottom 40. The seat back 38 may be supported by the seat bottom 40 and may be stationary or movable relative to the seat bottom 40. The seat back 38 and the seat bottom 40, may be adjustable in multiple degrees of freedom. Specifically, the seat back 38 and the seat bottom 40 may themselves be adjustable, in other words, adjustable components within the seat back 38 and/or the seat bottom 40, and/or may be adjustable relative to each other.

The seat bottom 40 and/or the seat back 38 may include a frame 42. The frame 42 may include tubes, beams, etc. The frame 42 may be formed of any suitable plastic material, e.g., carbon fiber reinforced plastic (CFRP), glass fiber-reinforced semi-finished thermoplastic composite (organosheet), etc. As another example, some or all components of the frame 42 may be formed of a suitable metal, e.g., steel, aluminum, etc. A cushion 44 is supported on the seat frame 42. The cushion 44 may be made of cushioning material covered with upholstery. The cushioning material may be formed of foam or any other suitable supportive material. The upholstery may be formed of cloth, leather, faux leather, or any other suitable material. The upholstery may be stitched in panels around the foam. Occupants typically sit on the seat cushion 44 of the seat bottom 40 and rest against the seat back 38.

The vehicle 22 may include one or more vibrators 24 that can be actuated to cancel or attenuate vehicle 22 vibration (acceleration) and prevent or minimize motion sickness of one or more occupants of the vehicle 22. Each vibrator 24 generates vibration, e.g., upon receipt of a command from the computer 28 specifying such vibration. The vibration may be at a specified frequency and/or amplitude. Each vibrator 24 may include, for example, an electric motor operatively coupled to an offset mass. Torque from the electric motor may rotate the offset mass and generate vibration. As another example, each vibrator 24 may include a mass that is urged to linearly oscillate within the vibrator 24, e.g., with a spring and electromagnet. Oscillation of the mass may generate vibration. Other conventional vibrators 24 may be used.

One or more vibrators 24 may be supported by each of the seats 36. For example, the vibrator 24 may be supported within the cushion 44 of the seat bottom 40, e.g., underneath where an occupant would sit in such seat 36. The vibrator 24 may be fixed to the frame 42 of the seat 36, e.g., via fastener or the like. The vibrator 24 may be fixed to a leg of the seat frame 42. As another example, the vibrator 24 fixed to the vehicle body 34 e.g., via fastener or the like. The vibrator 24 may be fixed to a floor 46 of the body 34 of the vehicle 22, e.g., proximate the seat 36 such that vibration is mechanically transferred from the floor 46 to the seat 36. For example, the vibrator 24 may be fixed to the body 34 at place where the frame 42 of seat 36 is connected to the body 34 of the vehicle 22.

The vehicle 22 may include a suspension system for controlling movement of the body 34 of the vehicle 22 relative to wheels 32 of the vehicle 22, e.g., a rear suspension 48 at a rear of the vehicle 22 and a front suspension 50 at a front of the vehicle 22. The rear suspension 48 may include a transversely extending rear axle assembly (not shown) adapted to operatively support the right and left rear wheels 32 of the vehicle 22. The rear axle assembly may be operatively connected to the body 34 by two damper systems 52. The front suspension 50 may include a transversely extending front axle assembly (not shown) to operatively support the right and left front wheels 32 of the vehicle 22. The front axle assembly may be operatively connected to the body 34 by another two damper systems 52. The term "damper system" as used herein refers to spring/damper systems in general and thus includes, for example, MacPherson struts, independent front suspension systems, and/or independent rear suspension systems.

Each of the damper systems 52 may include a damper 54 and a spring 56, e.g., a helical coil spring. The dampers 54 may be arranged within the springs 56, e.g., in a coil-over arrangement. The dampers 54 may be spaced apart from the springs 56. The dampers 54 serve to dampen the relative motion of the unsprung portion of the front suspension 50 and rear suspension 48 and the sprung portion (i.e., the body 34) of the vehicle 22 by applying a damping force to the vehicle 22 that opposes the relative motion of the unsprung portion of the front suspension 50 and rear suspension 48 and the sprung portion of the vehicle 22. The springs 56 apply a biasing force to the sprung portion of the vehicle 22, which supports the sprung portion of the vehicle 22 on the unsprung portion of the front suspension 50 and rear suspension 48 in such a manner that bumps and other impacts are absorbed by the front suspension 50 and rear suspension 48.

The active dampers 30 may be positioned with, next to, integrated into, or near the dampers 54. When activated, the active dampers 30 apply an active force, e.g., an extension force or a compression force, on the vehicle 22 to soften or firm up the front suspension 50 and/or the rear suspension 48, e.g., in response to a command from the computer 28. Generally, the active force operates in a substantially parallel direction to the biasing force of the springs 56. For example, during cornering, the active dampers 30 of the damper systems 52 on the outside of the turn may be operated to apply an active force to the vehicle 22 to help keep the vehicle 22 level, or otherwise control body angle, during the turn. The active dampers 30 actively control body movements of the vehicle 22 independently of the damping forces generated by the dampers 54. In other words, the active dampers 30 operate in parallel with the dampers 54 to control the ride and handling of the vehicle 22. The active dampers 30 may also vary a ride height at each corner of the vehicle 22. The active dampers 30 may be, for example, hydraulic active dampers, electromagnetic active dampers, of another suitable type of active of semi-active dampers. The active dampers 30 may each include an actuator that provide the active force. The actuators may be linear actuators that increases (by extending) or decreases (by compressing) a distance between ends in response to an instruction from the computer 28. The actuator may be, for example, a pneumatic actuator, a piezoelectric actuator, and/or an electromechanical actuator. The actuator may convert rotary motion of an electric motor into linear displacement via screws and/or gears, e.g., with leadscrews, screw jacks, ball screws, roller screws, etc. The actuator may utilize hydraulic pressure to move a piston disposed within a hollow cylinder filled with an incompressible fluid. Pressure may be provided to the fluid with a pump. Similarly, the actuator may utilize pneumatic pressure.

Additionally or alternatively, one or more characteristics of the active dampers 30 (e.g., damping coefficient) can be controlled to cancel or attenuate vehicle vibration and prevent or minimize motion sickness of one or more occupants of the vehicle 22. In various implementations, one or more of the active dampers 30 may be used in place of the vibrators 24 and the vibrators 24 may be omitted. The vibrators 24 may additionally or alternatively be mounted to the body 34 of the vehicle 22 near the wheels 32, respectively (e.g., as in FIG. 1). The active dampers 30 may serve as the vibrators 24.

The vehicle 22 includes sensors 26. The sensors 26 may detect internal states of the vehicle 22, for example, wheel speed, wheel orientation, and engine and transmission variables. The sensors 26 may detect the position or orientation of the vehicle 22, for example, global positioning system (GPS) sensors; accelerometers such as piezo-electric or microelectromechanical systems (MEMS) sensors; gyroscopes such as rate, ring laser, or fiber-optic gyroscopes; inertial measurements units (IMU); and magnetometers. The sensors 26 may detect the external world, for example, radar sensors, scanning laser range finders, light detection and ranging (LIDAR) devices, and image processing sensors such as cameras. The sensors 26 may include communications devices, for example, vehicle-to-infrastructure (V2I) or vehicle-to-vehicle (V2V) devices. The sensors 26 may be supported at one or more positions in or on the body 34 of the vehicle 22. The sensors 26 may be configured to detect objects including, but not limited to, other vehicles, road hazards (e.g., debris, potholes, etc.), pedestrians and cyclists, curbs or other road infrastructure, etc. For example, a plurality of sensors 26 may be arranged on a front and rear portion of the vehicle 22 to scan the environment (e.g., the road) in front of and/or behind the vehicle 22, respectively, and may be arranged on sides of the vehicle 22 to scan the environment next to the vehicle 22.

One or more sensors 26 are configured to measure vibration of the vehicle 22. The measured vibration may include an amplitude and/or a frequency of the vibration of the vehicle 22. For example, the sensor 26 may include an accelerometer configured to measure vertical acceleration of the vehicle 22, i.e., acceleration in the vertical (Z) direction. The accelerometer may also measure acceleration in the longitudinal (Y) direction and acceleration in the latitudinal (X) direction. The accelerometer may be, for example, a three-axis accelerometer or another suitable type of acceleration sensor. In various implementations, three single axis accelerometers may be used to measure acceleration in the vertical, longitudinal, and lateral directions. The accelerometer may generate a vertical acceleration sample at predetermined periods/frequencies, such as each X milliseconds, where X is an integer greater than zero. The accelerometer may determine the amplitudes at the predetermined frequencies, for example, via a Fourier Transform (FT). The accelerometer may output an analog signal specifying detected accelerations. The accelerometer may be located at any suitable location, e.g., fixed to the body 34, the seat frame 42, etc.

The motion sickness control system 20 may include one or more biometric sensors 58. Biometric sensors 58 capture biometric information of one or more occupants of the vehicle 22. The biometric sensors 58 may include, for example, one or more cameras that capture images of eyes of an occupant (e.g., eye tracking) of the vehicle 22. The biometric sensors 58 may include one or more heartbeat sensors 26 that measure heart rate of an occupant. The biometric sensors 58 may include one or more brainwave sensors 26 that measure brain waves of an occupant. The biometric sensors 58 may include one or more perspiration sensors 26 that measure perspiration of an occupant.

The biometric data captured by the biometric sensors 58 can be used to determine whether one or more occupants of the vehicle 22 are experiencing symptoms of motion sickness. Feedback from the biometric sensors 58 can be used to adjust control of the vibrators 24 and/or the active dampers 30. For example, if data from the biometric sensors 58 indicates that an occupant of the vehicle 22 is experiencing symptoms of motion sickness, the vibrators 24 may be controlled to generate vibration to oppose the vertical acceleration and/or vibration and minimize or prevent motion sickness of the occupant. Additionally or alternatively, if data from the biometric sensors 58 indicates that an occupant of the vehicle 22 is experiencing symptoms of motion sickness, one or more characteristics of the active dampers 30 may be adjusted (e.g., damping coefficient) to minimize or prevent motion sickness of the occupant.

The biometric sensors 58 may be supported by, e.g., fixed to, the body 34 of the vehicle 22. For example, heartbeat sensors and/or perspiration sensors may be supported by a steering wheel of the vehicle 22. As another example, cameras may be supported by a pillar, dashboard, or other suitable passenger cabin component.

The biometric sensor 58 may be remote from, and communicate wirelessly, with the vehicle 22. For example, one or more perspiration sensors, brainwave sensors, and heartbeat sensors may be supported by a wearable electronic device 60 wirelessly connected to the computer 28 of the vehicle 22, e.g., connected via Bluetooth, WiFi, etc. Example wearable electronic devices 60 include smart phones, smart watches, fitness trackers, ear buds, and smart patches.

The vehicle 22 may include a navigation system 62. The navigation system 62 is implemented via circuits, chips, or other electronic components that can determine a present location of the vehicle 22. The navigation system 62 may be implemented via satellite-based system such as the Global Positioning System (GPS). The navigation system 62 may triangulate the location of the vehicle 22 based on signals received from various satellites in the Earth's orbit and/or using road attributes with mapped references. The navigation system 62 is programmed to output signals representing the present location of the vehicle 22 to, e.g., the computer 28 via a communication network 64. In some instances, the navigation system 62 is programmed to determine a route from the present location to a future location, including developing alternative routes if a road is flooded. The navigation system 62 may access a virtual map stored in the memory (discussed below) and develop the route according to the virtual map data.

The communication network 64 includes hardware, such as a communication bus, for facilitating communication among components of the vehicle 22. The communication network 64 facilitates wired or wireless communication among the components, e.g., the active dampers 30, the computer 28, the sensors 26, the vibrators 24, the biometric sensors 58, etc., in accordance with a number of communication protocols such as controller area network (CAN), Ethernet, WiFi, Local Interconnect Network (LIN), and/or other wired or wireless mechanisms.

Figure 4:
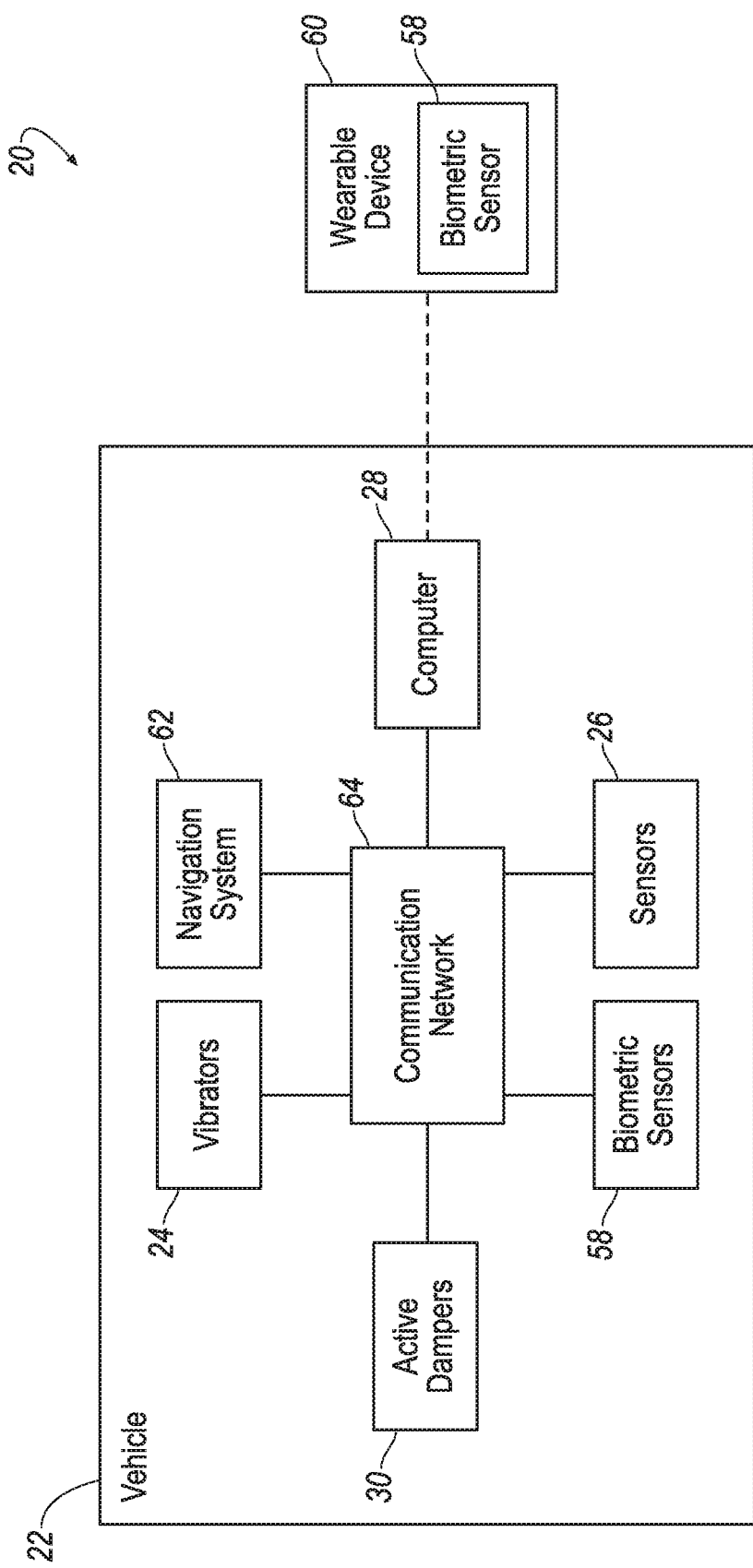
FIG. 4 is a block diagram of components of the vehicle and the motion sickness control system.

The computer 28, implemented via circuits, chips, or other electronic components, is included for carrying out various operations, including as described herein. The computer 28 is a computing device that generally includes a processor and a memory, the memory including one or more forms of computer-readable media and storing instructions executable by the processor for performing various operations, including as disclosed herein. The memory of the computer 28 further generally stores remote data received via various communications mechanisms; e.g., the computer 28 is generally configured for communications on a controller area network (CAN) bus or the like, and/or for using other wired or wireless protocols, e.g., Bluetooth, etc. The computer 28 may also have a connection to an onboard diagnostics connector (OBD-II). Via the communication network 64 using Ethernet, WiFi, the CAN bus, Local Interconnect Network (LIN), and/or other wired or wireless mechanisms, the computer 28 may transmit messages to various devices and/or receive messages from the various devices, e.g., the sensors 26, the biometric sensors 58, the vibrators 24, the active dampers 30, the wearable electronic device 60, etc. Although one computer 28 is shown in FIG. 4 for ease of illustration, it is to be understood that the computer 28 could include, and various operations described herein could be carried out by, one or more computing devices.

The computer 28 may be programmed to, i.e., the memory stores instructions executable by the processor to, determine whether a vertical acceleration and/or vibration of the vehicle 22 is within a threshold rate at which motion sickness commonly occurs. The threshold rate may include a frequency and an amplitude. The computer 28 may determine whether the vertical acceleration and/or vibration of the vehicle 22 is within the threshold rate at which motion sickness commonly occurs based on data from the sensors 26, e.g., based on data from one or more accelerometers. For example, the computer 28 may determine the vertical acceleration has at least a predetermined amplitude at one or more of the predetermined frequencies where motion sickness may occur or within a predetermined frequency range within which motion sickness may occur. The predetermined amplitudes, frequencies, and/or frequency ranges may be empirically determined, e.g., such that motion sickness may occur if the amplitude at one of the predetermined frequencies or within the predetermined frequency range has at least the predetermined amplitude. The predetermined frequency range may be calibratable and may be, for example, approximately 0.01-0.9 Hertz (Hz) or another suitable range where motion sickness may occur. The predetermined frequencies may be, for example, 0.5 Hz, 0.55 Hz, 0.6 Hz, 0.65 Hz, 0.7 Hz, 0.75 Hz, and 0.8 Hz and/or one or more other suitable frequencies where motion sickness may occur.

The computer 28 is be programmed to determine whether data from the biometric sensor 58 is indicative of motion sickness. The computer 28 may determine the data from the biometric sensor 58 is indicative of motion sickness by comparing a characteristic detected by the biometric sensor 58 with a threshold. For example, the computer 28 may determine a heart rate detected by a heart rate sensor is indicative of motion sickness when the detected heart rate is greater than a threshold heart rate. As another example, the computer 28 may determine the detected heart rate is indicative of motion sickness when the detected heart rate increases by more than a threshold amount within a specified amount of time. As another example, the computer 28 may determine that eye movement of an occupant identified in images from the camera is indicative of motion sickness when a rate of eye moment, i.e., a number of eye movements with a specified amount of time, is greater than a threshold rate of eye movement. The computer 28 may identify eyes of the occupant, and respective eye movement, using, for example, conventional image recognition techniques. As another example, the computer 28 may determine an amount and/or rate of perspiration detected by a perspiration sensor is indicative of motion sickness when the detected amount and/or rate of perspiration is greater than a perspiration threshold. As yet another example, the computer 28 may determine brainwave activity detected by a brainwave sensor is above a brainwave threshold. The brainwave activity may be in a specified area of the brain. The computer 28 may use other techniques to determine whether the biometric sensor 58 is indicative of motion sickness.

The thresholds and for the various characteristics used by the computer 28 to determine whether data collected by the biometric sensor 58 is indicative of motion sickness may be predetermined and stored in memory. For example, heart rate data, eye movement data, perspiration data, and/or brainwave data may be collected for a sample population of occupants not experiencing motion sickness and for a sample population of occupants experiencing motion sickness. The data for the sample populations may be compared to identify differences therebetween, and one of more thresholds may be based on such differences.

The computer 28 may be programmed to set a vibrator target. The computer 28 may set the vibrator target (e.g., frequency and/or amplitude) to minimize or prevent the possibility of motion sickness by attenuating the measured vibration of the vehicle 22. The computer 28 may set the vibrator target to cancel or attenuate the vertical acceleration at that one of the predetermined frequencies. For example only, when the amplitude of the vertical acceleration at one of the predetermined frequencies (one of the predetermined frequencies or a frequency within the predetermined frequency range) is greater than the predetermined amplitude, the computer 28 may set the vibrator target to indicate (1) that one of the predetermined frequencies as a target frequency and (2) an amplitude and sign that is opposite that of the vertical acceleration at that frequency as a target amplitude. For example, if the vertical acceleration at 0.7 Hz is +4, the computer 28 may set the vibrator target to 0.7 Hz and −4 to attenuate or cancel the vertical acceleration being experienced at 0.7 Hz. While the example of using an amplitude that is equal and opposite to the vertical acceleration at the same frequency is provided, a different amplitude and/or a different frequency may be used. The same or similar may be performed for each one or more frequencies where the amplitude of the vertical acceleration is greater than the predetermined amplitude. The computer 28 may set the vibrator target based on the amplitudes, respectively. For example, the computer 28 may determine the vibrator target using a lookup table or an equation stored in memory that relates amplitudes (and signs) at the predetermined frequencies to target amplitudes (and signs) at the predetermined frequencies. The vibrator target may include the one or more target amplitudes (and signs) to vibrate the vibrators 24 at the predetermined frequencies. The look up table and/or equation may be predetermined, for example, based on empirical testing of sample populations of occupant at various frequencies and amplitudes than indicates which frequencies and amplitudes are likely to cause motion sickness.

The computer 28 may be programmed to set a damper target. The computer 28 may set the damper target (e.g., damping coefficient) to minimize or prevent the possibility of motion sickness by attenuating the measured vibration of the vehicle 22. The computer 28 may determine the damper target, for example, based on the vertical acceleration and/or the vibrator target. The computer 28 may set the damper target, for example, using one of an equation and a lookup table that relates vertical acceleration and/or vibrator targets to damper targets (e.g., damping coefficients). The look up table and/or equation may be predetermined, for example, based on empirical testing of sample populations of occupant at various frequencies and amplitudes than indicates which frequencies and amplitudes are likely to cause motion sickness, and based on empirical or computer modeling of responsiveness of the vehicle in attenuating vibration and/or vertical sickness at various dampening coefficients.

The computer 28 may be programmed to selectively adjust the vibrator target and/or the damper target, respectively, based on biometric information from one or more of the biometric sensors 58. For example, the computer 28 may adjust the vibrator target (target amplitude and/or target frequency) when the biometric information from one or more of the biometric sensors 58 is indicative of the possibility of motion sickness by an occupant of the vehicle 22. Additionally or alternatively, the computer 28 may adjust the damper target when the biometric information from one or more of the biometric sensors 58 is indicative of the possibility of motion sickness by an occupant of the vehicle 22.

The computer 28 may be programmed to set a body angle target (i.e., an amount of forward/rearward tilt and/or right/left tilt of the body 34, e.g., relative to level with a horizon). The computer 28 may set the body angle target to cancel or attenuate lateral and/or longitudinal forces experienced by an occupant of the vehicle 22 which may cause motion sickness. Such forces may, for example, be generated when the vehicle 22 executes a maneuver, e.g., turns, travels a curved road, changes lanes, swerves to avoid an obstacle, accelerates, brakes, etc. The computer 28 may identify the lateral forces based on data from the sensors 26, e.g., from an accelerometer. The computer 28 may identify the lateral and/or longitudinal forces based on a predicted trajectory of the vehicle 22. The predicted trajectory may be provided by the navigation system 62, determined by the computer 28 (e.g., using conventional autonomous/semi-autonomous path planning and obstacle avoidance techniques), etc. The predicted trajectory may identify an upcoming maneuver that will generate lateral and/or longitudinal force. For example, a steering angle and/or turn radius (e.g., needed to maneuver the predicted trajectory) and a speed of the vehicle 22 may be used to calculate lateral and/or longitudinal forces. The computer 28 may set the body angle target based on the lateral and/or longitudinal forces. For example, the computer 28 may determine the body angle target using a lookup table or an equation that relates lateral and/or longitudinal forces to body angle targets. The look up table and/or equation may be predetermined, for example, based computer modeling of an occupant of a vehicle. The computer model may take include account forces applied to a modeled occupant, including modeled internal forces (e.g., applied to vertebrae, hip bones, inner ear structures, etc.), from acceleration of the vehicle 22, e.g., when performing a maneuver and/or traveling along a predicted trajectory. The computer model may also take into account normal forces applied to the modeled occupant, e.g., from a modeled seat having a modeled seat bottom and seat back. The model may be used to calculate target body angles that position the modeled seat such that the normal forces from the modeled seat counteract the forces from acceleration of the vehicle 22.

The computer 28 is programmed to actuate the vibrators 24. The computer 28 may actuate the vibrators 24 by transmitting a command to the vibrators 24, e.g., via the communication network 64. The command may specify a frequency and/or amplitude of vibration for the vibrator 24 to produce. The computer 28 may actuate the vibrators 24 based on the vibrator target. More specifically, the computer 28 may actuate the vibrators 24 such that the vibrators 24 vibrate at the frequency (or frequencies) and/or amplitude (or amplitudes) specified in the vibrator target. The computer 28 may actuate the vibrators 24 to vibrate at the target amplitudes (and signs) at the predetermined frequencies.

The computer 28 is programmed to actuate the active dampers 30. The computer 28 may actuate the active dampers 30 by transmitting a command to the active dampers 30, e.g., via the communication network 64. The command may specify a dampening coefficient, a length, an extension force, or a compression force. The computer 28 may actuate the active dampers 30 based on the damper target. For example, the computer 28 may actuate the active dampers 30 to achieve the dampening coefficient of the damper target. The computer 28 may actuate the active dampers 30 based on the body angle target. For example, the computer 28 may command the actuators to provide various lengths, extension forces, and/or compression forces such that the body 34 of the vehicle 22 achieves the body angle target and attenuates lateral and/or longitudinal acceleration experienced by the occupant along the predicted trajectory.

The computer 28 may actuate the vibrators 24 and/or active dampers 30 upon determining a vertical acceleration and/or vibration of the vehicle 22 is within a threshold rate at which motion sickness commonly occurs. The computer 28 may actuate the vibrators 24 and/or active dampers 30 upon determining data from the biometric sensor 58 is indicative of motion sickness. The computer 28 may actuate the vibrators 24 and/or active dampers 30 upon determining that images from the camera include predetermined eye movement indicative of motion sickness. The computer 28 may actuate the vibrators 24 and/or active dampers 30 upon determining that a heart rate detected by the heart rate sensor includes a predetermined characteristic indicative motion sickness, e.g., the detected heart rate is above a threshold heart rate and/or the detected heart rate increases by more than a threshold amount within a specified amount of time. The computer 28 may actuate the vibrators 24 and/or active dampers 30 upon determining that brainwaves detected by the brainwave sensor include a predetermined characteristic indicative of motion sickness, e.g., brainwave activity detected by the brainwave sensor is above a brainwave threshold. The computer 28 may actuate vibrators 24 and/or active dampers 30 upon determining that perspiration detected by the perspiration sensor includes a predetermined characteristic indicative of motion sickness, e.g., detected amount of perspiration and/or rate of perspiration is greater than a perspiration threshold.

Figure 5:
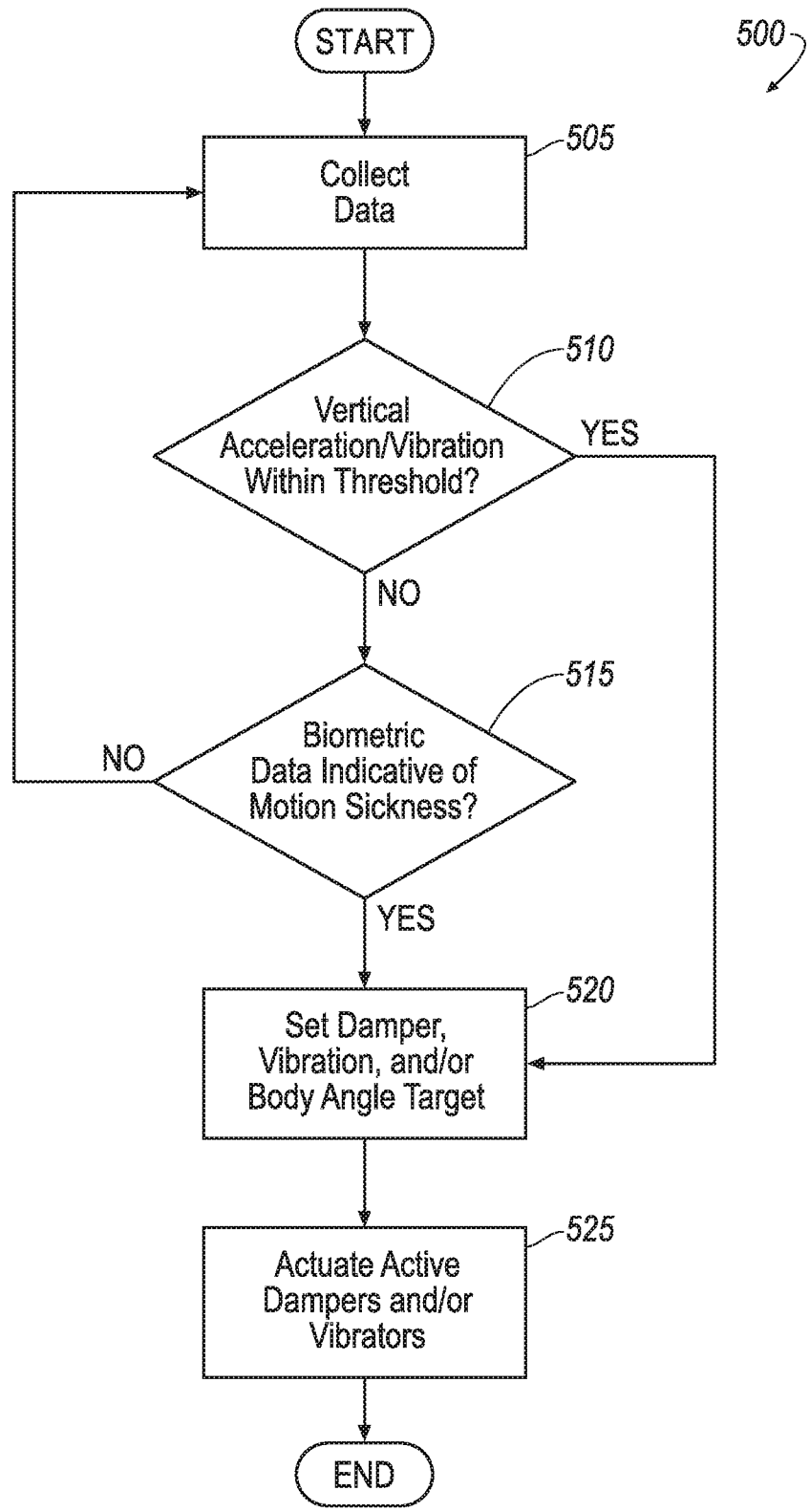
FIG. 5 is a flowchart illustrating a process for controlling the motion sickness control system.

FIG. 5 is a process flow diagram illustrating an exemplary process 500 for controlling the vehicle 22 to minimize or prevent motion sickness by one or more vehicle occupants. The process 500 begins in a block 505 where the computer 28 collects data, e.g., from the sensors 26, the biometric sensors 58, the navigation system 62, etc. The computer 28 may collect data substantially continuously and/or at intervals. The intervals may be at the predetermined frequencies, e.g., 0.5 Hz, 0.55 Hz, 0.6 Hz, 0.65 Hz, 0.7 Hz, 0.75 Hz, and 0.8 Hz and/or one or more other suitable frequencies where motion sickness may occur.

Next, at a block 510 the computer 28 determines whether a vertical acceleration and/or vibration of the vehicle 22 is within a threshold rate which motion sickness commonly occurs, e.g., based on data from one or more sensors 26 such as an accelerometer that measures acceleration in the vertical direction. The computer 28 may determine the vertical acceleration and/or vibration of the vehicle 22 is within the threshold rate when the vertical acceleration has at least a predetermined amplitude at one or more of the predetermined frequencies where motion sickness may occur or within a predetermined frequency range within which motion sickness may occur, e.g., as described herein. Upon determining the vertical acceleration and/or vibration of the vehicle 22 is not within the threshold rate the process 500 moves to a block 515. Upon determining the vertical acceleration and/or vibration of the vehicle 22 is within the threshold rate the process 500 moves to a block 520.

At the block 515 the computer 28 determines whether data from a biometric sensor 58 is indicative of motion sickness. The computer 28 may determine the data from the biometric sensor 58 is indicative of motion sickness by comparing a characteristic detected by the biometric sensor 58 with a threshold, e.g., as described herein. Upon determining the data from a biometric sensor 58 is indicative of motion sickness the process 500 moves to the block 520. Upon determining data from a biometric sensor 58 is not indicative of motion sickness the process 500 returns to the block 505. Alternately, the process 500 may end.

At the block 520 the computer 28 sets at least one of a vibrator target, a damper target, and/or a body angle target to minimize or prevent the possibility of motion sickness by attenuating the measured vibration of the vehicle 22 and/or other accelerations experienced by an occupant. The computer 28 may set the vibrator target, the damper target, and/or the body angle target based on data from the sensors 26, based on a predicted trajectory of the vehicle 22, with a lookup table, and/or with an equation, e.g. as described herein. The computer 28 may execute a process 600 (discussed below) to set the vibrator target.

Next, at a block 525 the computer 28 actuates the active dampers 30 and/or the vibrators 24, e.g., by transmitting commands to the active dampers 30 and/or the vibrators 24. The computer 28 may actuate the vibrators 24 such that the vibrators 24 vibrate at the frequency (or frequencies) and/or amplitude (or amplitudes) specified in the vibrator target set at the block 520. The computer 28 may actuate the active dampers 30 to achieve the dampening coefficient of the damper target set at the block 520. The computer 28 may actuate the active dampers 30 to achieve the body angle target set at the block 520. After the block 525 the process may end. Alternately, the process 500 may return to the block 505.

Figure 6:
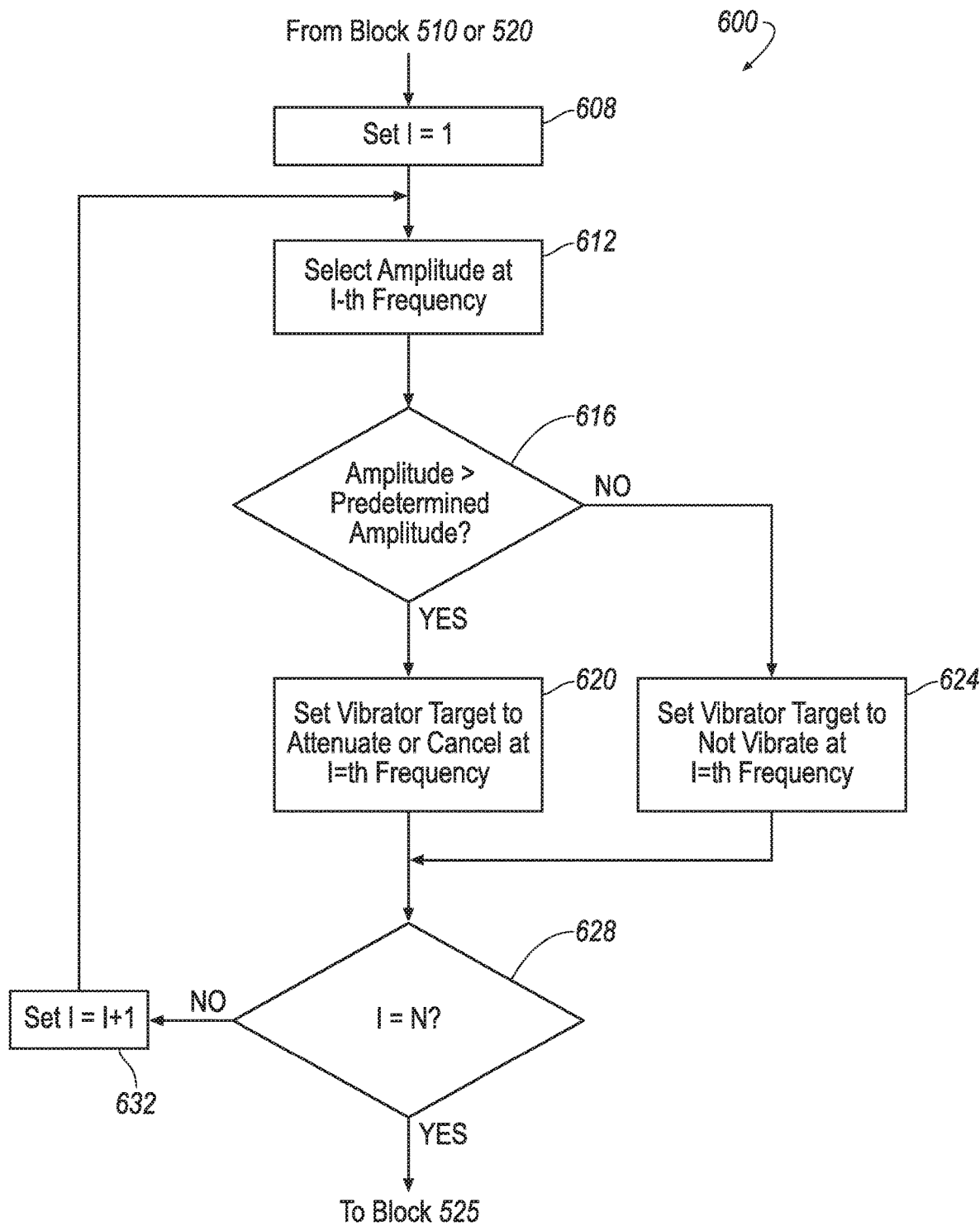
FIG. 6 is a flowchart illustrating a process for setting a vibrator target for use in the process of FIG. 5.

FIG. 6 is a process flow diagram illustrating an exemplary process 600 for setting a vibrator target. The process 600 begins in a block 608, e.g., when executing block 520 of the process 500. At the block 608 the computer 28 sets a counter value (I) equal to 1.

Next, at a block 612 the computer 28 selects the amplitude of the vertical acceleration at the I-th one of the predetermined frequencies.

Next, at a block 616 determines whether the amplitude of the vertical acceleration at the I-th one of the predetermined frequencies is greater than the predetermined amplitude. Upon determining the amplitude of the vertical acceleration at the I-th one of the predetermined frequencies is greater than the predetermined amplitude the process 600 moves to a block 620. Upon determining the amplitude of the vertical acceleration at the I-th one of the predetermined frequencies is not greater than the predetermined amplitude the process 600 moves to a block 624.

At the block 620 the computer 28 determines the vibrator target for the I-th one of the predetermined frequencies based on the amplitude at the I-th one of the predetermined frequencies. For example, the computer 28 may determine the vibrator target for the I-th one of the predetermined frequencies using a lookup table or an equation that relates amplitudes (and signs) to target amplitudes (and signs). The vibrator target may also include the one or more target amplitudes (and signs) to vibrate the vibrators 24 at other ones of the predetermined frequencies. After the block 620 the process 600 moves to a block 628.

At the block 624 the computer 28 may set the target amplitude for the I-th one of the predetermined frequencies to zero. The vibrators 24 will not vibrate at the I-th one of the predetermined frequencies when the target amplitude at the I-th one of the predetermined frequencies is set to zero. After the block 624 the process 600 moves to the block 628.

At the block 628 the computer 28 determines whether counter value (I) is equal to N. N is an integer greater than zero and is equal to the total number of the predetermined frequencies. Upon determined the counter value (I) is not equal to N the process 600 moves to a block 632. Upon determined the counter value (I) is equal to N the computer 28 actuates vibrators 24 to vibrate at the target amplitudes (and signs) at the predetermined frequencies, respectively, as specified in the vibrator target, e.g., the computer 28 may execute the block 525 of the process 500.

At the block 632 the computer 28 increments the counter value (I) by 1 and returns to the block 612 for the next one of the predetermined frequencies.

With regard to the processes described herein, it should be understood that, although the steps of such processes have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the description of the processes herein is provided for the purpose of illustrating certain embodiments and should in no way be construed so as to limit the disclosed subject matter.

Computing devices, such as the computer 28 generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. Some of these applications may be compiled and executed on a virtual machine, such as the Java Virtual Machine, the Dalvik virtual machine, or the like. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

In some examples, system elements may be implemented as computer-readable instructions (e.g., software) on one or more computing devices (e.g., servers, personal computers, computing modules, etc.), stored on computer readable media associated therewith (e.g., disks, memories, etc.). A computer program product may comprise such instructions stored on computer readable media for carrying out the functions described herein.

The terms "in response to," "when," and "upon" herein specify a causal relationship in addition to a temporal relationship.

The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

What is claimed is:

1. A motion sickness control system for a vehicle, the motion sickness control system comprising:
   a vibrator;
   a sensor configured to measure vibration of the vehicle;
   a seat, the vibrator supported by the seat; and
   a computer having a processor and a memory storing instructions executable by the processor to actuate the vibrator at a target frequency based on the measured vibration of the vehicle, wherein the target frequency attenuates the measured vibration of the vehicle; and
   wherein the sensor is configured to measure an amplitude of the vibration of the vehicle, and wherein the instructions include instructions to actuate the vibrator at the target frequency upon determining the amplitude of the vibration is greater than a predetermined amplitude.

2. The motion sickness control system of claim 1, wherein the seat includes a seat bottom having a cushion, and wherein the vibrator is supported within the cushion.

3. The motion sickness control system of claim 1, wherein the seat includes a frame, and wherein the vibrator is fixed to the frame.

4. The motion sickness control system of claim 1, further comprising a vehicle body, the vibrator fixed to the vehicle body.

5. The motion sickness control system of claim 1, wherein the sensor is configured to measure a frequency of the vibration of the vehicle, and wherein the instructions include instructions to actuate the vibrator at a target amplitude based on the measured amplitude and frequency of the vibration.

6. The motion sickness control system of claim 1, further comprising a biometric sensor, and wherein the instructions include instructions to actuate the vibrator upon determining data from the biometric sensor is indicative of motion sickness.

7. The motion sickness control system of claim 6, wherein the biometric sensor is a camera configured to capture images of eyes of an occupant of the vehicle, and wherein the instructions include instructions to actuate the vibrator upon determining that images from the camera include predetermined eye movement indicative of motion sickness.

8. The motion sickness control system of claim 6, wherein the biometric sensor is a heart rate sensor configured to measure a heart rate of an occupant of the vehicle, and wherein the instructions include instructions to actuate the vibrator upon determining that a heart rate detected by the heart rate sensor includes a predetermined characteristic indicative of motion sickness.

9. The motion sickness control system of claim 6, wherein the biometric sensor is a brainwave sensor configured to measure brainwaves of an occupant of the vehicle, and wherein the instructions include instructions to actuate the vibrator upon determining that brainwaves detected by the brainwave sensor include a predetermined characteristic indicative of motion sickness.

10. The motion sickness control system of claim 6, wherein the biometric sensor is a perspiration sensor configured to measure perspiration of an occupant of the vehicle, and wherein the instructions include instructions to actuate the vibrator upon determining that perspiration detected by the perspiration sensor includes a predetermined characteristic indicative of motion sickness.

11. The motion sickness control system of claim 1, further comprising an active damper, and wherein the instructions include instructions to actuate the active damper at a damper target based on the measured vibration of the vehicle, wherein the damper target attenuates the measured vibration of the vehicle.

12. The motion sickness control system of claim 1, further comprising an active damper, and wherein the instructions include instructions to predict a trajectory of the vehicle and to actuate the active damper based on the predicted trajectory to reduce motion sickness of an occupant of the vehicle.

13. The motion sickness control system of claim 12, wherein the instructions include instructions to actuate the active damper to attenuate lateral acceleration experienced by the occupant along the predicted trajectory.

14. The motion sickness control system of claim 1, further comprising:
- an accelerometer configured to measure vertical acceleration of the vehicle;
- an active damper configured to damp vertical movement of a wheel of the vehicle; and
- wherein the instructions include instructions to actuate the active damper at a damper target based on the vertical acceleration detected by the accelerometer, wherein the damper target attenuates the measured vertical acceleration of the vehicle.

15. The motion sickness control system of claim 14, wherein the damper target includes a target damping coefficient, and wherein the instructions include instructions to control a damping coefficient of the active damper based on the target damping coefficient.

16. The motion sickness control system of claim 14, wherein the instructions include instructions to predict a trajectory of the vehicle and to actuate the active damper based on the predicted trajectory to reduce motion sickness of an occupant of the vehicle.

17. The motion sickness control system of claim 16, wherein the instructions include instructions to actuate the active damper to attenuate lateral acceleration experienced by the occupant along the predicted trajectory.

* * * * *